(12) United States Patent
Supper et al.

(10) Patent No.: US 6,572,647 B1
(45) Date of Patent: Jun. 3, 2003

(54) METHOD OF MAKING A STENT

(75) Inventors: Wolfgang Supper, Karlsruhe (DE); Walter Gamer, Bruchsal (DE); Thomas Kirchhoff, Walzbachtal (DE)

(73) Assignee: Angiomed GmbH & Co. Medizintechnik KG, Karlsruhe (DE)

( * ) Notice: Subject to any disclaimer, the term of this patent is extended or adjusted under 35 U.S.C. 154(b) by 0 days.

(21) Appl. No.: 09/565,004

(22) Filed: May 4, 2000

(30) Foreign Application Priority Data

Oct. 29, 1999 (DE) .......................... 199 52 295

(51) Int. Cl.$^7$ ................................. A61F 2/06
(52) U.S. Cl. ...................... 623/1.15; 623/1.16
(58) Field of Search .................. 623/1.22, 1.1, 623/1.11, 1.15, 1.18, 1.19, 1.16; 219/121.67, 121.68, 121.6

(56) References Cited

U.S. PATENT DOCUMENTS

| | | | |
|---|---|---|---|
| 5,514,154 A | * | 5/1996 | Lau et al. .................. 606/1.18 |
| 5,716,393 A | | 2/1998 | Lindenberg et al. |
| 5,776,161 A | | 7/1998 | Globerman |
| 5,780,807 A | | 7/1998 | Saunders |
| 5,800,520 A | | 9/1998 | Fogarty et al. |
| 5,913,897 A | * | 6/1999 | Corso, Jr. et al. ............ 623/1.1 |
| 6,042,597 A | * | 3/2000 | Kveen et al. ................ 623/1.1 |

FOREIGN PATENT DOCUMENTS

| | | |
|---|---|---|
| CA | 2155527 | 8/1994 |
| DE | 2544371 | 4/1976 |
| DE | 19539449 | 4/1997 |
| DE | 29522101 U1 | 1/2000 |
| DE | 19901530 | 7/2000 |
| DE | 19921530 | 7/2000 |
| DE | 69521346 T2 | 4/2002 |
| EP | 0688545 | 12/1995 |
| EP | 0712614 | 5/1996 |
| EP | 0790041 | 8/1997 |
| EP | 0792627 | 9/1997 |
| WO | WO 96/18359 | 6/1996 |

\* cited by examiner

Primary Examiner—Julian W. Woo

(57) ABSTRACT

A laser cut stent for transluminal delivery has windows in its cylindrical wall, the windows giving the stent enhanced flexibility during delivery along said lumen. A method of making such a stent involves removing from the wall of a tube enough material to leave the tube wall penetrated in a multiplicity of separate cut lines, in a pattern which permits the tube to expand. The tube is then expanded and then a plurality of tube wall scrap portions are removed from the tube wall between adjacent cut lines, thereby to introduce a plurality of spacings between adjacent stenting zones of the tube wall surface, these remaining after compression of the tube to a configuration to allow it to be advanced along a tortuous bodily lumen. Advantageously, the material of the tube is a shape memory alloy and the tube is for a self-expanding stent.

22 Claims, 2 Drawing Sheets

METHOD OF MAKING A STENT

FIELD OF THE INVENTION

This invention relates to a method of making for transluminal delivery a stent of working radius R from a tube of radius r and wall thickness T, smaller than R, the method comprising the steps of removing material from the tube wall with the tube at radius r, or substantially r, over the full wall thickness T to leave the tube wall penetrated in a multiplicity of separate cut lines, in a pattern which permits the tube to expand to radius R; expanding the tube to radius R; and performing at least one manufacturing step on the tube at radius R.

The invention also relates to stents which can be made in accordance with such methods.

BACKGROUND ART

It is well-known to make self-expanding stents for placement in bodily lumens by selecting a tube of Nitinol shape memory alloy, having a diameter appropriate for transluminal delivery, taking a length of the Nitinol tube corresponding to the desired length of the stent, mounting the tube length in a jig, and using a laser cutting device, under the control of a computer, to cut in the wall thickness T of the tube length a pattern of a multiplicity of full wall thickness cut lines parallel to the longitudinal axis of the tube length. All the cut lines are quite short in proportion to the tube length. All the cut lines are mutually parallel and have an ordered spacing throughout the length of the tube length. The cut lines are arranged in bands around the circumference of the tube length.

It is known, and advantageous, to select, for the band at each end of the stent, a cut length greater than the length of the cut lines present in the bands spaced from both ends of the stent. Other patterns of cut lines of different length can be adopted, to vary the mechanical properties of the stent along the length of the stent, as required by the particular task which the stent is to perform when placed in the body.

The cut lines of each alternate band are co-linear. The cut lines of each adjacent band are, in the circumferential direction, halfway between two adjacent cut lines of the adjacent band either side. Each band of cut lines overlaps with the cut lines of the adjacent band. In this way, the provision of the bands of cut lines enables the tube length to expand radially, with the material of the tube wall between the cut lines deforming and each cut line transforming into a diamond-shaped window in the wall of the tube.

For shape memory materials, it is necessary to impose on the tube length a "memory" of a shape which it is desired that the tube length should have, in its functioning as a stent, after placement in the bodily lumen. Thus, for Nitinol materials, it is known to expand the tube length, after laser cutting, over a mandrel, to bring it to the diameter which it is desired it should assume when placed in the bodily lumen. Held in that diameter, the tube length is then brought to a temperature sufficiently high to allow the molecular movements within the metal matrix which constitute the memory of the material. When the tube length is cooled, and the mandrel removed, the tube length remains in its expanded radius configuration. It can be compressed down to its original radius and captured within a sheath, for installation on the distal end of a delivery system, for transluminal delivery.

In many applications of such self-expanding stents, high flexibility of the stent, after placement in the bodily lumen, is required. That flexibility is achievable with Nitinol. However, there are applications when the stent has to be delivered through a tortuous bodily lumen, in which case, flexibility of the stent tube length, in its original radius, is also desirable.

An enhancement of flexibility, of the stent in its expanded diameter configuration, has been provided by the present applicant in its stent designs, by parting the material separating two adjacent diamond windows of a circumferential stenting band as described above. Thus, in one convenient arrangement, a parting line is made at two out of every three junctions between adjacent diamond openings in stenting band. The cut lines and parting lines are made by a laser device, so that the width of each cut line and parting line is very small, typically less than 0.06 mm.

SUMMARY OF THE INVENTION

The present inventors have found out that self-expanding Nitinol stents as described immediately above, while flexible in their expanded deployed configuration, still lack flexibility in the compressed configuration in which they are transluminally delivered, and that the degree of flexibility is not always sufficient for optimum delivery along tortuous lumens. It is therefore an object of the present invention to facilitate transluminal delivery of such stents by giving the stents an enhanced flexibility when in the compressed, small radius, configuration.

The characterising features of one aspect of the present invention are set out in claim 1 below.

Expressed very simply, material is removed from the tube length, when the tube length is at its large radius configuration, so that the tube length when compressed down to its small radius configuration for transluminal delivery exhibits a plurality of windows. It is these windows which endow the tube length with enhanced flexibility when in the compressed configuration.

For the purposes of understanding the present invention, it is important to appreciate the inter-relationship between the window cutting step and the step of the giving the tube length a memory of the configuration it is required to take up. Laser cutting the starting length of tube is a precision operation in which the computer controlled laser cutting device needs a detailed programme and a fixed starting point of reference on the tube length. It would of course be a simple modification of the laser cutting programme to require the laser to make the transverse parting lines necessary for the subsequent creation of the desired windows. However, one still has the task of bringing the tube length from its original radius r to its end radius R, there to give it a memory of this large radius configuration. Once the parting lines and windows have been laser cut into the wall of the tube length, only a few remaining bridges between adjacent stenting bands prevent the tube length from falling into pieces. Such an entity has less resources to survive expansion on a mandrel from small radius r to large radius R. Accordingly, with the present invention, the designated scrap portions, corresponding to the windows, are not broken away until after the tube length has been expanded to its large radius R.

Choosing not to make the parting lines in the initial laser cutting operation has repercussions for manufacturing efficiency, as follows. The step of expanding the tube length to its large radius has the consequence that the reference point for,the laser cutting equipment is lost, and the expansion on the mandrel gives the stent precursor an individual configuration which varies from tube length to tube length, so that a second computer controlled laser cutting step, in order to part the scrap portions from the material of the tube length, would appear to require fresh calibration. Instead, the present applicant arranges for each scrap portion to be parted from the material of the tube length, at the large radius R as a manual operation. For the time being, this step is not automated.

Nevertheless, steps can be taken to facilitate the manual operation, notably by having the laser, in the initial cutting programme, make blind cuts through the wall thickness of the tube length, which are transverse to the basic cut lines, but which fall short of extending all the way between two adjacent cut lines defining an intervening scrap portion. These blind cuts serve to define the parting lines at which each scrap portion will be parted from the tube length later. For example, if the laser cuts partly, but not wholly through, the strut radial thickness between two cut lines, it has proved to be relatively easy for an operative, using forceps, to pull out each scrap portion held only by a residual frangible portion at the blind end of each blind cut.

Self-expanding stents are known, which exhibit a plurality of stenting bands, arranged end to end along the length of the stent, and each joined to the adjacent stenting band by a bridging band. These bridging bands are often more flexible than the intervening stenting bands, but less effective in resisting tissue stenosis. With the present invention, the scrap portions can be found at locations in the stent which are serving as bridges between adjacent stenting zones, with removal of selected scrap portions reducing the number of bridges between two adjacent stenting zones, and thereby increasing flexibility between these two adjacent stenting zones.

An alternative construction of self-expanding stent sees a continuous helical stenting zone running from one end of the stent to the other, with a helical bridging zone coterminous with the stenting helix. Analogously, the scrap portions can correspond to bridging struts in the bridging helix between adjacent turns of the stenting helix, with the removal of these scrap portions again tending to increase flexibility between adjacent turns of the stenting helix.

Regardless what pattern of stenting zones and bridging zones the tube length exhibits, it will normally be the case that the laser cutting operation creates a pattern of cells in the wall of the tube length, the unit cell being characteristic of the stent and defining its performance.

It is normal to perform polishing steps on self-expanding Nitinol stent precursors, when all cutting operations have been completed. A polishing step is of particular significance for the stent precursors of the present invention, because of the need to remove any rough fracture surfaces where the scrap portions have been removed after laser cutting.

For a better understanding of the present invention, and to show more clearly how the same may be carried into effect, reference will now be made to the accompanying drawings.

DETAILED DESCRIPTION OF THE PREFERRED EMBODIMENT

Figure 1:
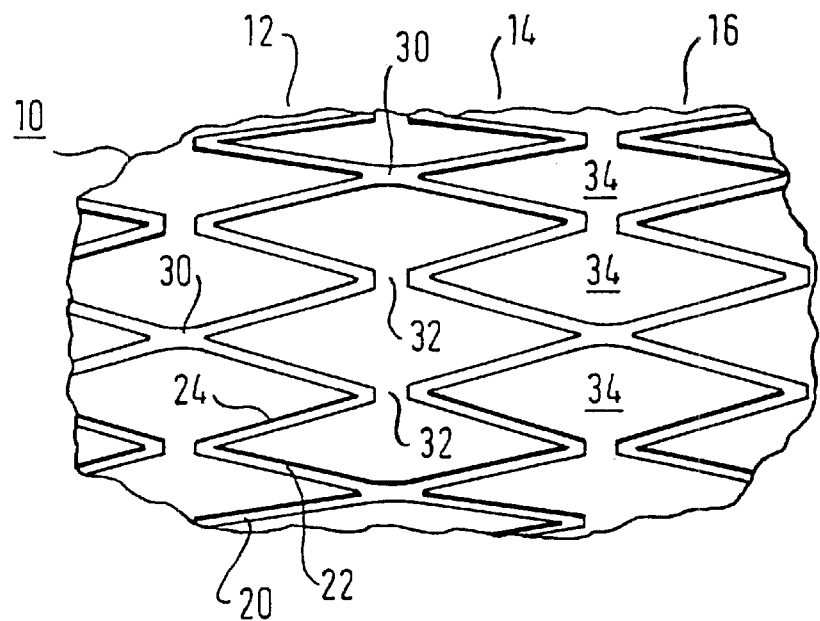
FIG. 1 is a view of part of the circumference of a stent in accordance with the present invention.

FIG. 1 shows part of a tube length 10, expanded to its operational radius R to exhibit successive stenting bands 12, 14, 16, of which typically there are about 20 over the length of the tube which forms the stent. Each stenting band 12, 14 is formed from a zigzag pattern of struts 20, 22, 24 of Nitinol shape memory alloy material. These struts have the thickness of the Nitinol tube from which the stent was made, and a width which is, in one embodiment, 0.2 mm. The wall thickness T of the tube can be the same or similar. Each zigzag stenting band 12, 14 is connected to an adjacent band on either side by a bridging zone 30, with one bridge every third strut, and alternate bridges to left and right of the zigzag band.

Some of the struts 20, 22, 24 are not linked by bridging zones 30 to adjacent stenting bands. Instead, they face the adjacent stenting band at a gap 32. It will be appreciated that the provision of twice as many gaps 32 as bridges 30, between adjacent zigzag stenting bands, gives enhanced flexibility for the stenting bands to move relative to each other, as the stent is flexed on its long axis. This helps the stent 10 to accommodate bodily movements, after deployment in surgery.

Considering still what is shown in FIG. 1, and imagining what happens to the zigzag bands when the stent is compressed to its original radius r, the reader will appreciate that each diamond window 34 transforms into a parallel-sided cut line of negligible width but of length slightly longer than the length of the diamond-shaped window 34. Significantly, a window 32 is still in evidence, between two adjacent cut lines. Importantly, the presence of these windows 32, when the tube length and stent are at their original radius r, endows the tube length, at radius r with a degree of flexibility, to bend on its longitudinal axis, which would not be present if the windows 32 were not present. Attention is now invited to drawing FIG. 2, in order to explain the origin of the windows 32.

Figure 2:
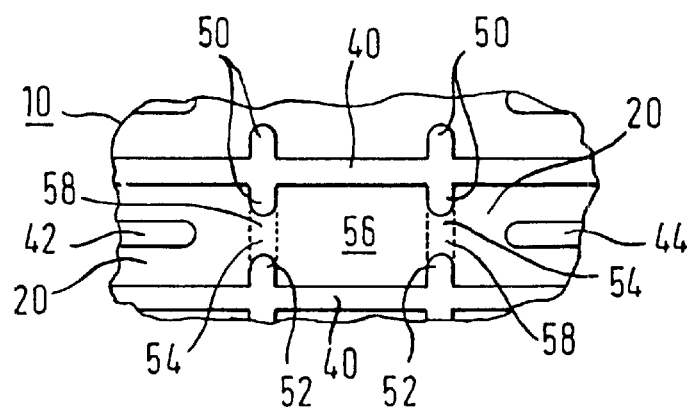
FIG. 2 is a detail of the tube length which is the precursor of the FIG. 1 stent, showing something of the pattern of laser cuts in the wall of the tube.

FIG. 2 shows a detail of the tube length in its original radius r, and something of the pattern of cuts made in the tube length 10 by the computer-controlled laser cutting operation on the original uncut Nitinol tube length.

The computer is programmed to cause the laser to execute a multiplicity of cut lines 40 which extend parallel to the length of the tube. Each cut line 40 defines the length dimension of a diamond window 34 of the patent shown in FIG. 1. Thus, the cut lines 40 are arranged in bands around the circumference of the tube length, with the cut lines 40 of each band being parallel and side by side, and all the cut lines in the bands spaced from both ends of the stent having the same length. The band at each end of the stent features longer cut lines. The cut lines of the band 42 adjacent to the left and the band 44 adjacent to the right lie circumferentially between adjacent cut lines 40, equally spaced from both, in order to form the next band of diamond windows of the expanded stent.

According to the present invention, however, the program for the laser cutting equipment also requires the laser to execute a pattern of four blind cuts communicating with each cut line 40 and facing the blind cuts 52 in the next adjacent cut line 40 of the band of cut lines, so that the blind cuts are arranged in pairs 50, 52 facing each other across the width of each strut 20, 22, 24 of the stent. These pairs of blind cuts 50, 52 define between their blind ends a parting zone 54 for a scrap portion 56 lying between two adjacent parting zones 54. It is in fact this scrap portion 56 which corresponds to the gap or window 32 shown in FIG. 1 and described above.

Optionally, and preferably, the laser cutting program is capable of scoring the stent material through each parting zone 54, in a score line 58 to less than the total radial thickness of the stent wall, to link two facing full depth blind cuts 50, 52. This makes it easier to break away manually the material of each scrap portion 56. Preferably, the power of the laser is reduced to a lower value for making the score lines.

Once the programmed laser cutting operation has created the pattern of cuts shown in FIG. 2, at the tube radius r, the tube length can be expanded on a mandrel up to its larger radius R, to take up the pattern shown in FIG. 1 (except that, scrap portions 56 are present where FIG. 1 shows gaps 32). With the tube at its large radius R an operative using a forceps tool can carefully remove each scrap portion 56 to create corresponding gaps 32. After that, the tube length must be carefully polished to remove all rough fracture surfaces corresponding to the parting lines and zones 54.

Figure 3:
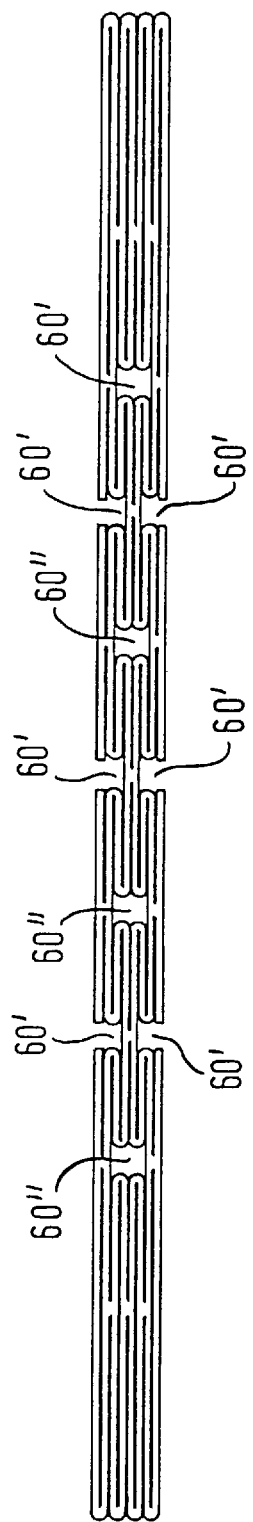
FIG. 3 is a long side view of a first embodiment of a stent in accordance with the invention showing the stent compressed.
Figure 4:
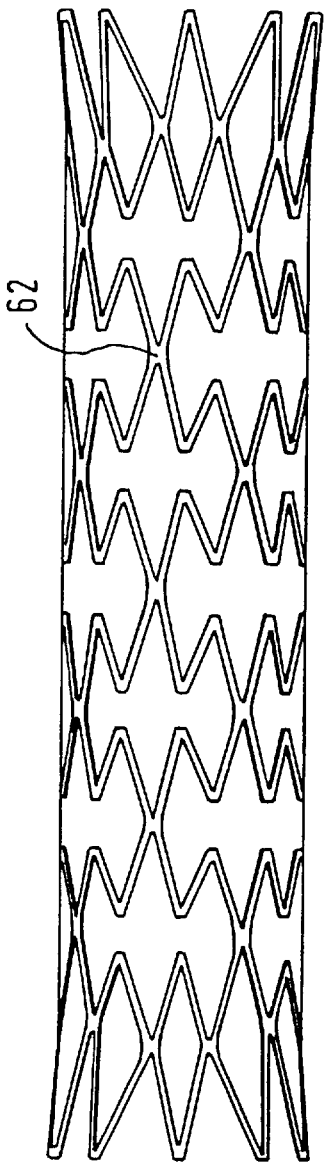
FIG. 4 is a similar view of a second embodiment of stent, showing the stent expanded.

Turning to FIGS. 3 and 4, one can see from FIG. 3 the places where material has been removed. Windows 60, each corresponding to two scrap zones 56, are marked in FIG. 3. Note the two windows 60' at mid-length on the stent, showing how easy it is for the stent to bend in the plane of the paper. Bending perpendicular to the plane of the paper is relatively easy at window 60" because there are in fact two such windows at each position shown, one above and one below the axis of the stent.

FIG. 4 shows a stent shorter than that of FIG. 3 and with slightly flared ends. In each band of diamond-shaped apertures, two out of every three obtuse angle diamond vertex 62 has been removed as a scrap portion 56, rendering the stent extremely flexible, both when compressed and when expanded.

Although the attached drawings show spaced separate stenting bands 12, 14, 16 separated by bridging bands 30, 32, it will be appreciated that the concept of the invention can be applied to a stent in which a helical bridging band separates adjacent turns of a helical stenting band which runs the length of the stent.

Self-expanding stents of shape memory alloy, made by laser cutting a sheet or tube, are useful in a wide range of stenting applications, such as in the bile duct and in blood vessels. The stents of the present invention are useful throughout this range, and especially where delivery to the stenting site is by advance along a tortuous delivery path. Indeed, the enhanced flexibility of the present stent, during delivery, may allow use of self-expanding stents in locations previously considered unreachable.

What is claimed is:

1. A method of making a transluminal stent of working radius R from a tube of radius r and wall thickness T, smaller than R, the method comprising the steps of:

a) removing material from the tube,wall with the tube at radius r, or substantially r, over the full wall thickness T to leave the tube wall penetrated in a multiplicity of separate cut lines, in a pattern which permits the tube to expand to radius R;

b) expanding the tube to radius R; and c) performing at least one manufacturing step on the tube at radius R;

d) comprising parting from the tube between adjacent parting lines a plurality of tube wall scrap portions, each lying between adjacent ones of said cut lines, thereby to introduce a plurality of spacings between adjacent stenting zones of the tube wall surface, said spacings remaining after compression of the tube to radius r, and giving the compressed tube an enhanced ability to bend along its long axis, as when it is advanced along a tortuous bodily lumen.

2. A method according to claim 1 wherein the stent is a self-expanding stent.

3. A method according to claim 1 wherein the tube comprises a shape memory alloy.

4. A method according to claim 3 wherein the shape memory alloy is Nitinol.

5. A method according to claim 1, further comprising: the step of defining said parting lines of each said scrap portion by at least one blind cut through the wall thickness of the tube which blind cut falls short of extending all the way between the cut lines which bound the scrap portion.

6. A method according to claim 5 wherein the cut lines are parallel to the axis of the stent and the blind cuts extend transverse to said axis.

7. A method according to claim 6 wherein each said scrap portion bridges between two adjacent stenting zones, spaced axially from each other.

8. A method according to claim 7 wherein each said stenting zone is a stenting band which extends around the circumference of the tube.

9. A method according to claim 7 wherein said stenting zones lie within a continuous helical band which is defined within the tube wall.

10. A method according to claim 7, 8 or 9 wherein said cut lines define a multiplicity of like cells which collectively constitute said stenting zones, or each of said stenting bands.

11. Method according to claim 10 wherein a multiplicity of axially extending bridges connect axially adjacent ones of said cells, and selected ones of the bridges correspond to said scrap portions so that, with parting of the scrap portions, a lesser number of bridges connect adjacent stenting zones.

12. A method according to claim 11 wherein the bridges collectively define at least one band of bridges extending circumferentially around the tube.

13. A method according to claim 11 wherein the bridges collectively define a helix lying within the tube and extending over at least a substantial part of the length of the tube.

14. A method according to claim 11, wherein the scrap portions are parted from the tube wall one by one, by a manual work step.

15. A method according to claim 11, further comprising: the step of polishing surface portions of the tube wall which constitute parting surfaces contiguous with the scrap portions.

16. A method according to claim 5 wherein the cuts are created by laser energy.

17. A method of making a stent for transluminal delivery to a site of surgery, which includes the step of laser cutting a pattern of cut lines in the wall thickness of a tube, some of the cut lines extending only partly through the tube wall to define, in part, scrap portions of the tube wall adapted for removal from the tube wall independently of said cutting step, the method comprising the further step of removing scrap portions from the tube wall for enhanced flexibility of the stent during delivery of the lumen.

18. As an intermediate article in the manufacture of a laser cut stent for transluminal delivery, a stent including a plurality of radially expandable circumferential members with adjacent circumferential members being joined to each other by a plurality of bridging bands, some of the bridging bands having weakened regions, the weakened regions being frangible separately from the laser cutting of the stent, whereby the weakened regions, when separated define windows in the cylindrical wall of the stent, said windows giving the stent enhanced flexibility during delivery along said lumen.

19. A stent as claimed in claim 18 comprising a shape memory alloy.

20. A stent as claimed in claim 18 wherein the windows are arranged in bridging bands spaced from each other, along the length of the stent, by stenting bands.

21. A stent as claimed in claim 18 wherein the windows are arranged in a helical pattern extending along the length of the stent, with a stenting helix lying between the turns of the window helix.

22. A stent as claimed in claim 18 wherein the distribution of windows varies along the length of the stent, to give the stent more flexibility between its ends than at its ends.

* * * * *